US007047977B2

(12) United States Patent
Frank

(10) Patent No.: US 7,047,977 B2
(45) Date of Patent: *May 23, 2006

(54) MEDICAL DEVICE FOR OVERCOMING AIRWAY OBSTRUCTION

(76) Inventor: Simon Frank, 3821 Southern Orchid Rd. North, Davie, FL (US) 33328

( * ) Notice: Subject to any disclaimer, the term of this patent is extended or adjusted under 35 U.S.C. 154(b) by 0 days.

This patent is subject to a terminal disclaimer.

(21) Appl. No.: 11/125,381

(22) Filed: May 8, 2005

(65) Prior Publication Data

US 2005/0199246 A1   Sep. 15, 2005

Related U.S. Application Data

(63) Continuation-in-part of application No. 10/901,720, filed on Jul. 29, 2004, now Pat. No. 6,926,007, which is a continuation-in-part of application No. 10/610,399, filed on Jun. 30, 2003.

(51) Int. Cl.
*A61F 13/00*   (2006.01)

(52) U.S. Cl. .................................. 128/846; 128/869
(58) Field of Classification Search ............... 128/846, 128/845, 870; 602/5, 41–44
See application file for complete search history.

(56) References Cited

U.S. PATENT DOCUMENTS

| 5,494,048 | A | 2/1996 | Carden |
| 5,515,867 | A * | 5/1996 | Lamb ........................ 128/845 |
| 6,196,224 | B1 | 3/2001 | Alfery |
| 6,200,285 | B1 | 3/2001 | Towliat |
| 2004/0084053 | A1 * | 5/2004 | Hess ........................ 128/870 |

* cited by examiner

*Primary Examiner*—Henry Bennett
*Assistant Examiner*—Shumaya B. Ali
(74) *Attorney, Agent, or Firm*—Ruben Alcoba, Esq.

(57) ABSTRACT

A medical device for overcoming upper airway obstruction when a patient is placed in a supine position, featuring a flat rectangular support base that attaches to the support frame perpendicularly, and a variation of lower jaw supports that attach to the support frame after encircling the patient's lower jaw.

6 Claims, 19 Drawing Sheets

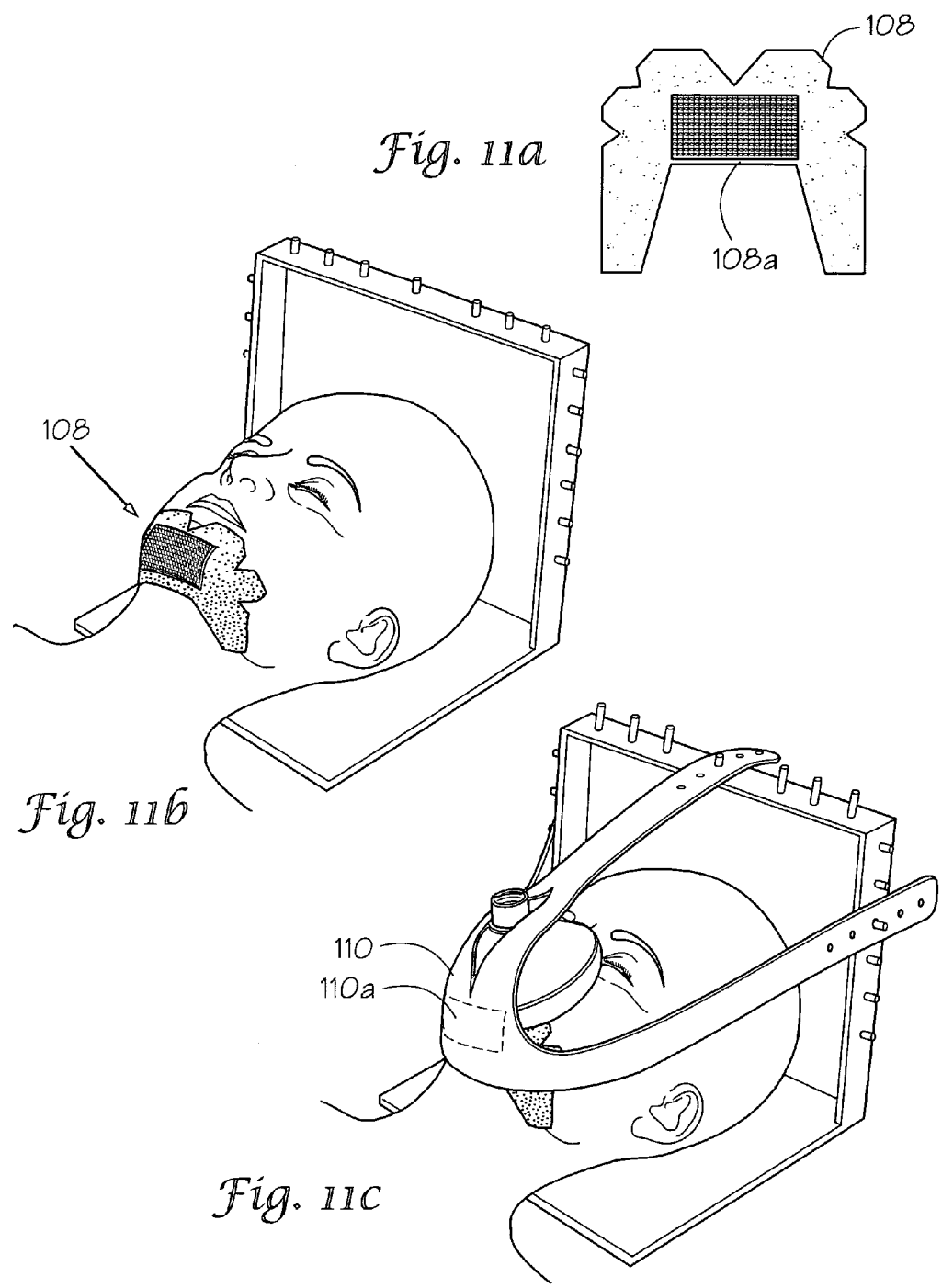

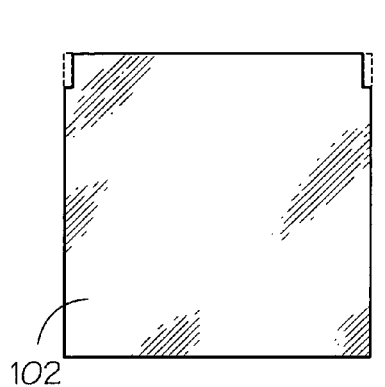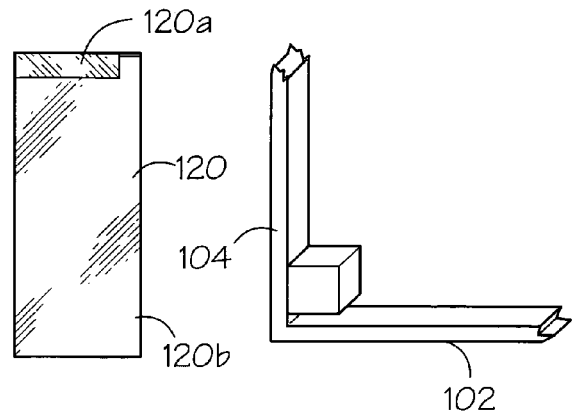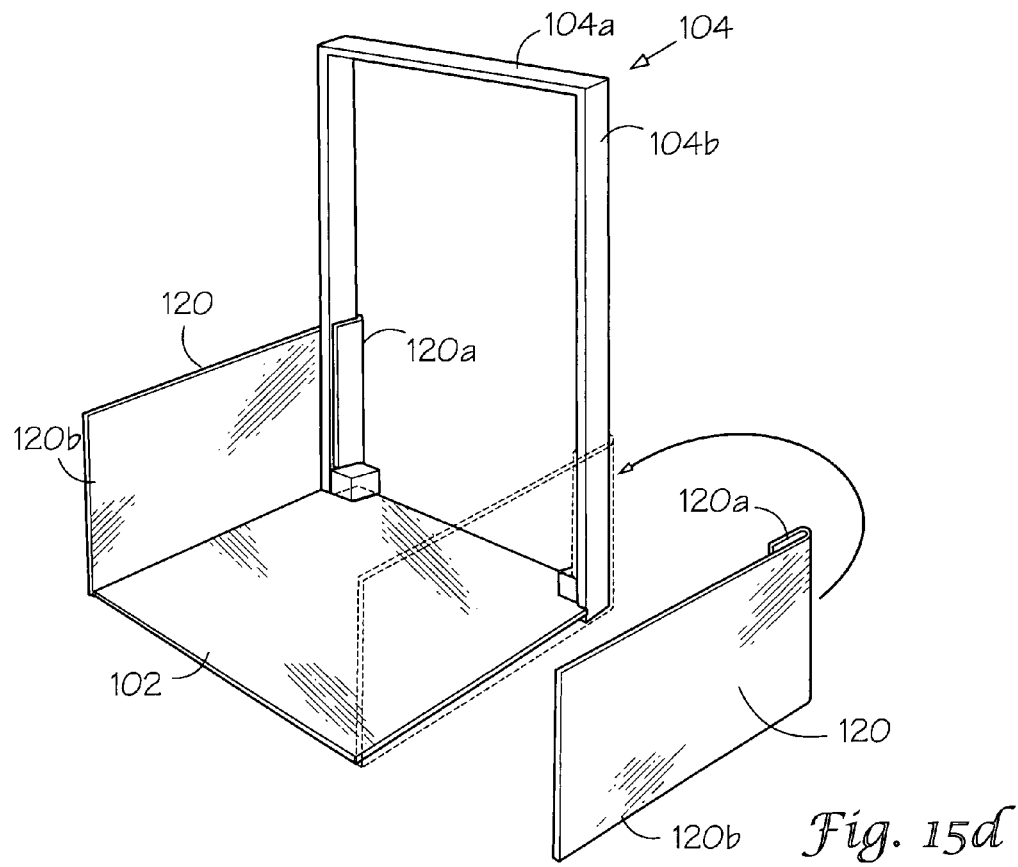

1

MEDICAL DEVICE FOR OVERCOMING AIRWAY OBSTRUCTION

CROSS REFERENCES

The present application is a continuation in part of my application Ser. No. 10/901,720 filed Jul. 29, 2004, now U.S. Pat. No. 6,926,007 entitled "Medical Device for Overcoming Airway Obstruction," which is a continuation of my application Ser. No. 10/610,399 filed Jun. 30, 2003, currently pending. All of these applications are incorporated herein by this reference which are not admitted to be prior art with respect to the present invention by their mention in the background.

BACKGROUND

Obstruction of the upper airway by the tongue is a common complication when a sedated or unconscious patient is lying in the supine position. The causes of unconsciousness may be sedation, anesthesia, head trauma, drug overdose or any of a multitude of medical causes. The patient may be in any emergency situation. The direct cause is that gravity pulls the person's tongue downwards (towards the cervical spine) and the tongue obstructs the airway and impedes respiration, partially or completely. The airway obstruction discussed above might cause a life-threatening situation if the airway obstruction is not urgently cleared, for hypoxemia and death can quickly ensue.

Anesthesiologists commonly overcome airway obstruction by tilting the patient's head backwards and pulling the chin up towards the ceiling and away from the body (cephalad). Obstruction of the airway is overcome because the base of the tongue is attached to the mandible, and by pulling the chin upward the tongue will be simultaneously pulled upward. This practice is very fatiguing and restricts the anesthesiologist's or emergency responder's ability to perform other functions that require two free hands.

An upper airway can also be maintained open by inserting various medical tubes into the airway, for example, nasal-pharyngeal, oral-pharyngeal, laryngeal mask airway (LMA) and the cuffed oral pharyngeal. But as of today, there are no medical devices in common use that attach externally to the face that will maintain an open upper airway.

In the past, medical personnel have attempted to use surgical tape to attempt to maintain an open upper airway. Anesthesiologist would secure tape around the chin of a patient and then attach the ends of the tape to an operating room table. Tape procedures are unsatisfactory, for the tape attachment pulls back and downwards and do not provide the upward pull required on the chin to maintain an open upper airway. Tape quickly stretches and traction is lost. Tape is not sufficiently adherent to cope with the traction forces and detaches. Other complications with this procedure are skin trauma and eye damage. The tape passes close to the patient's eyes and contact with the eye is unavoidable if the patient coughs or turns the head. The method of attaching tape to the operating room table cannot be used to manage an obstructed airway outside of the operating room, example, at a roadside motor vehicle accident or during subsequent transportation to hospital.

Chin props comprising a ball on the end of an arm secured to the operating room table have also been used to push the chin up. They too have proven to be unsatisfactory and are not commonly used, because they are large and cumbersome and get in the way of surgeons operating on the upper body. Furthermore, if misapplied they may constrict the airway.

Chin props with complex mechanisms that attach to suitable operating tables, cannot be used to manage an obstructed airway outside of the operating room, for example, at a roadside motor vehicle accident or during subsequent transportation to hospital.

Information relevant to attempts to address these problems can be found in U.S. Pat. Nos. 5,494,048, 6,200,285 B1, and 6,196,224 B1. However, each one of these references suffers from one or more of the following disadvantages:

1. Can cause eye damage and skin trauma;
2. Require attachment to suitable operating tables;
3. Obstruct the attendant's view of the patient;
4. Do not provide sufficient upward leverage to the chin;
5. Do not lend themselves to use in accident situations;
6. Do not effectively overcome airway obstruction; and
7. Difficulties in removal of devices, should immediate endotracheal intubation be required.

Inside and outside the operating room, an urgent need exists for equipment that overcomes upper airway obstruction and maintains an open upper airway. This equipment should be compatible with and improve the effectiveness of oral-pharyngeal and nasal-pharyngeal airways and face masks. In the operating room, such equipment would allow mask anesthesia to be used for sedated and anesthetized patients instead of general anesthesia and endotracheal intubation with immediate cost savings. Outside the operating room, a need exists for portable, compact equipment that can overcome upper airway obstruction and maintain an open airway and that can be used in cramped quarters such as an ambulance, a hyperbaric chamber and an MRI chamber.

For the foregoing reasons, there is a need for a medical device is safe and reliable that will overcome upper airway obstruction and that will maintain an open airway in the anesthetized and sedated patient lying in a supine position in an operating room and any unconscious patient lying in the supine position at any site. To be effective, the equipment should be safe and easy to use and reliable. The equipment should free up the operators' hands; render oral and nasal pharyngeal airways more effective and not interfere with but facilitate the use of a face mask. The equipment should be free standing, compact and portable.

SUMMARY

The present invention is directed to a medical device that assists in overcoming airway obstruction and maintaining an open airway when a patient, who may or may not be anesthetized, is unconscious and placed in the supine position. This device satisfies the following needs:

1. It frees the practitioner's hands to do other tasks;
2. Does not obstruct the view and allows the practitioner to visually monitor the patient;
3. It is a compact and portable device;
4. It does not cause eye damage or skin trauma;
5. Does not require the use of specific operating room tables when operating the device; and
6. Allows for the easy removal of the device should the patient vomit or emergency endotracheal intubation be required.

The medical device for overcoming airway obstruction comprises of a rectangular cradle that has first and second portions, wherein the first portion has a length that is at least a distance that allows a patient's head to rest on and act as an anchor to the cradle and the second portion has a length that is at least a distance that allows a band to be placed under a patient's chin and encircle the second portion so that an upward pull can be generated on the chin by the band when the second portion is placed in a perpendicular position to the first portion, and the cradle's width is at least a distance that allows for the clearance of a patient's side facial features when the patient's head rests on the first portion of the cradle and a band is made to encircle the chin of a patient and attach to the second portion of the cradle; and a band that attaches to the second portion of the cradle when the second portion is perpendicular to the first portion.

One of the many advantages of this invention is the simplicity of its construction. The fact that the two main elements of this invention are a perpendicular portions and a band that can be easy attached to one of the portions of the plate after encircling the chin of a patient whose head rests on the other portion of the cradle after being placed in a supine position, attest to the simplicity of construction and use of this device. This invention takes precautions in preventing injuries that have been previously caused by the prior art, for example, eye damage or skin trauma. This invention also aids those in the emergency transportation field, for they need to have the maximum use of their hands when dealing with other aspects of emergency situations facing them. In addition, not having to worry whether the patient is breathing properly can allow emergency personnel to care for other injuries sustained by the patient and to attend to other patients.

A further advantage to this invention is that it is a stand-alone medical device. The device does not need to be attached to any supporting devices to become operable. When a patient's head is made to rest on one of the surfaces of the perpendicular portion, the weight of the patient's head on the portion is sufficient to secure the cradle so that an upward pull on the chin created between a band attached to the sides of the cradle not carrying the weight of the patient's head and the patient's chin will be maintained during the use of this device. Remember, as long as this upward pull is maintained, the upper airway will be maintained open, thus it is key that the tension created with this device not be compromised and this is easily solved by using the weight of the patient's head as the anchor to the device.

Yet another advantage to this invention is the placement of the band on the second portion insures that the band does not come in contact with the patient's eyes, this is very important for one cannot prevent coughing and other involuntary movements of the head.

DRAWINGS

These and other features, aspects, and advantages of the present invention will become better understood with regard to the following description, appended claims, and drawings where:

FIG. 11a shows a chin pad;

FIG. 11b shows the chin pad of FIG. 11a placed on a patient in a supine position;

FIG. 11c shows the chin pad of FIG. 11a and patient of FIG. 11b in use with an anesthetic mask and the T-band of the present invention;

Figures 12A, 12B, 12C:
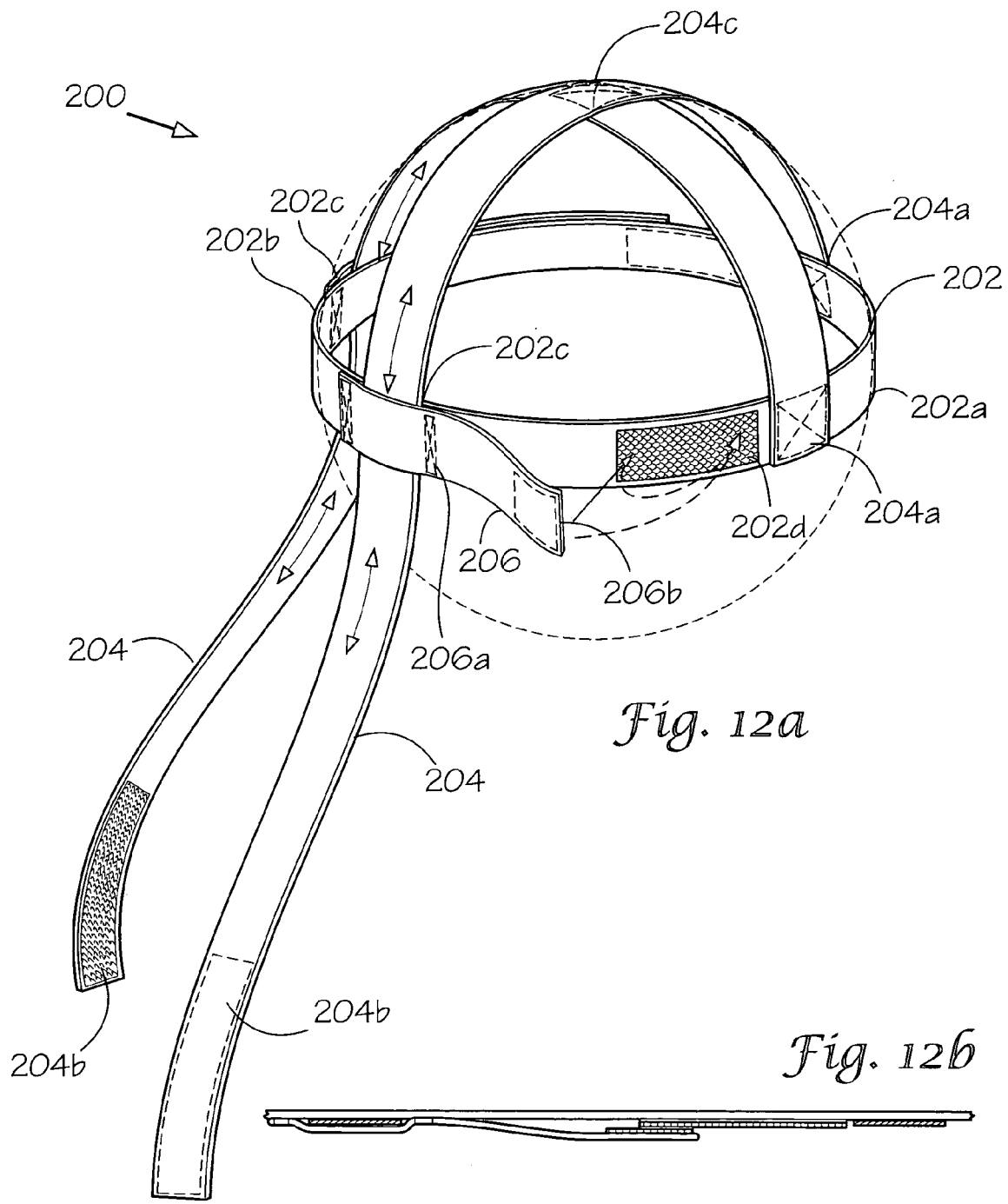
FIG. 12a shows a harness of another embodiment of the present invention.
Figure 12D:
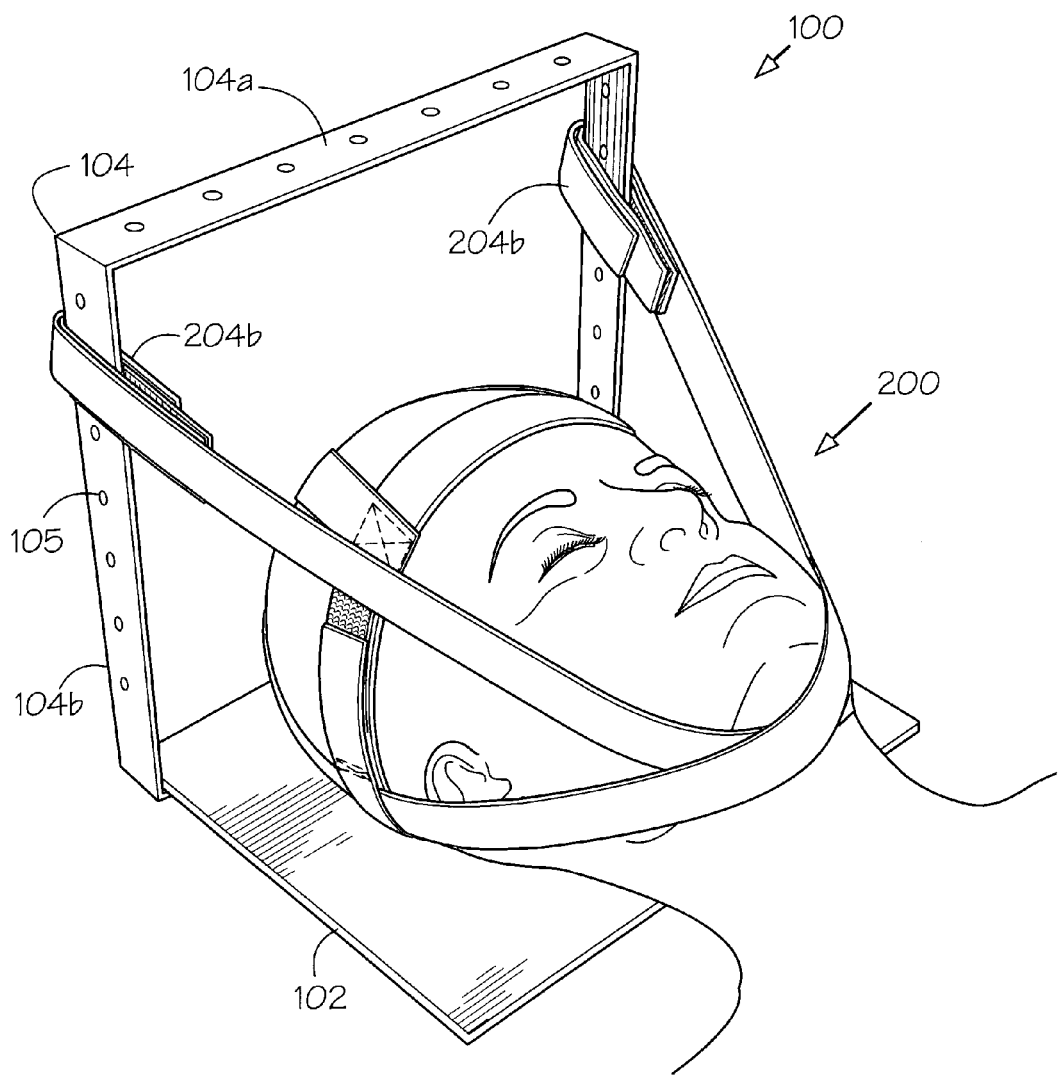
Figure 13A:
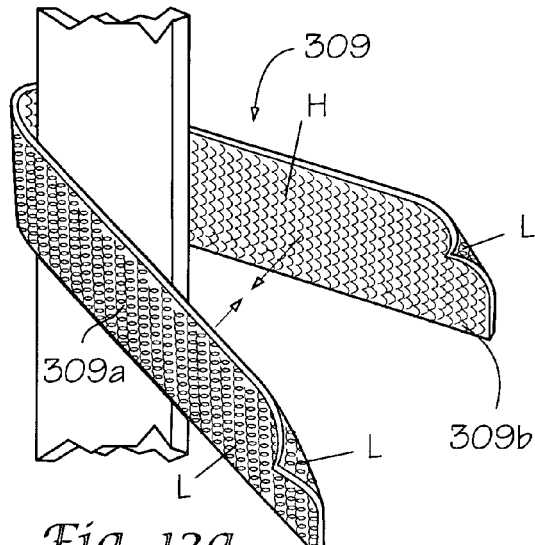
Figure 13B:
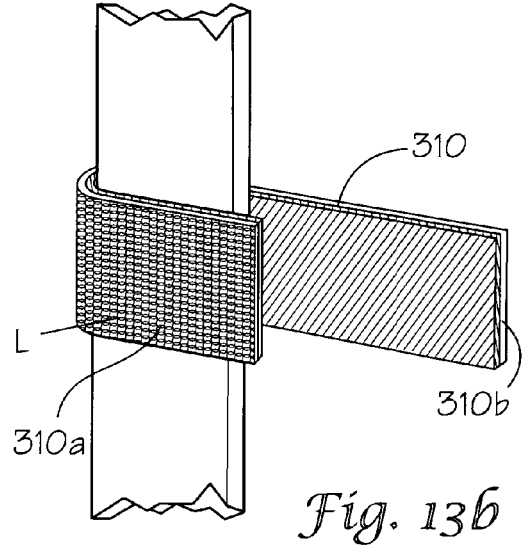
Figure 14A:
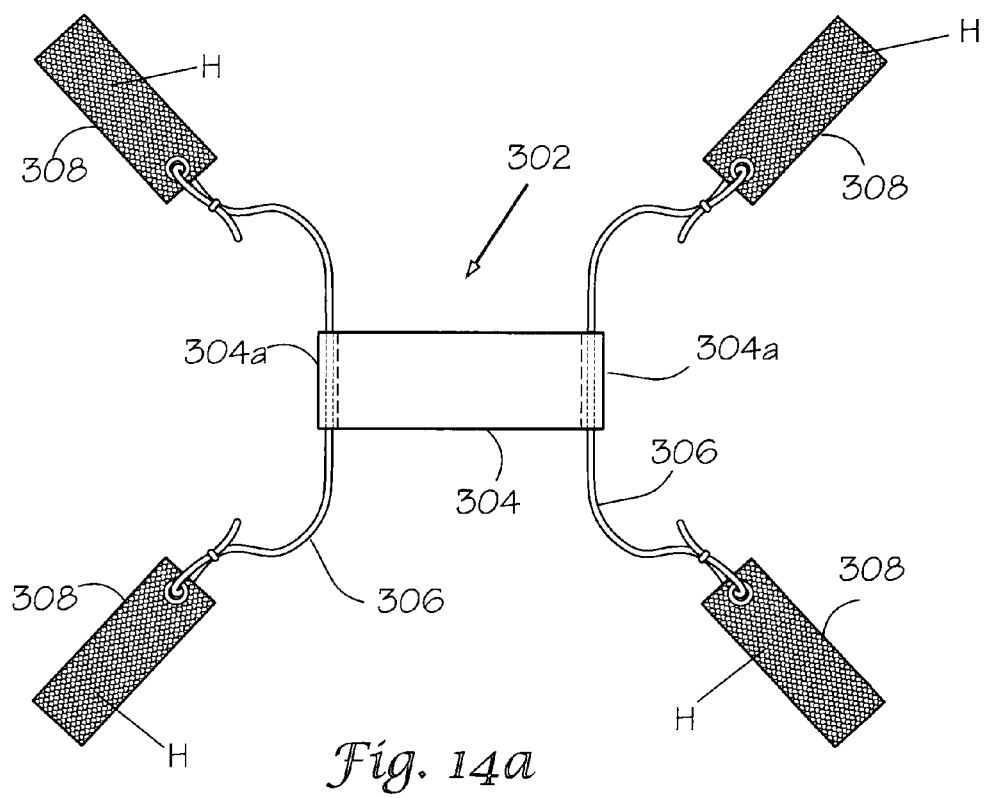
Figure 14B:
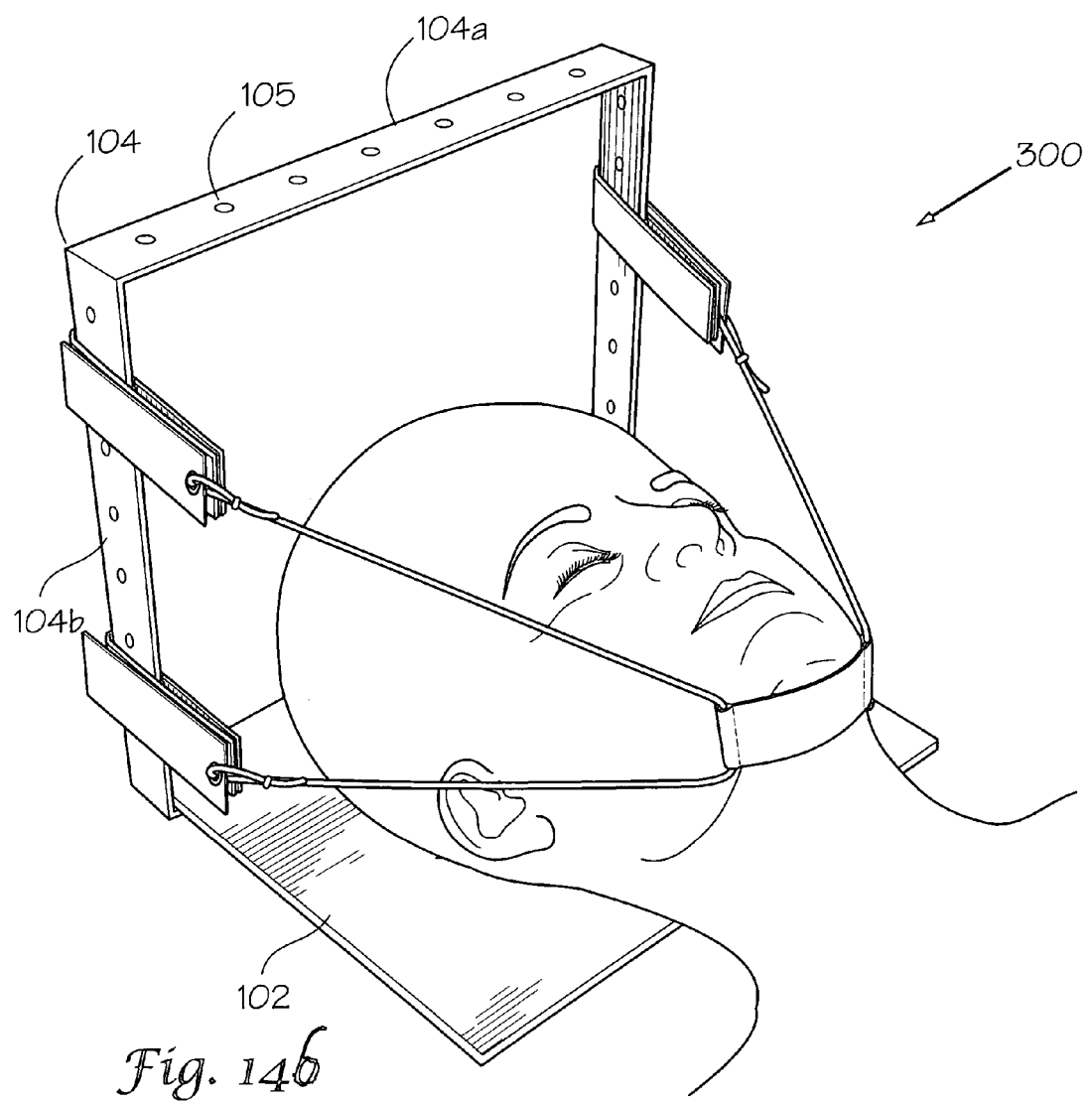
Figure 14C:
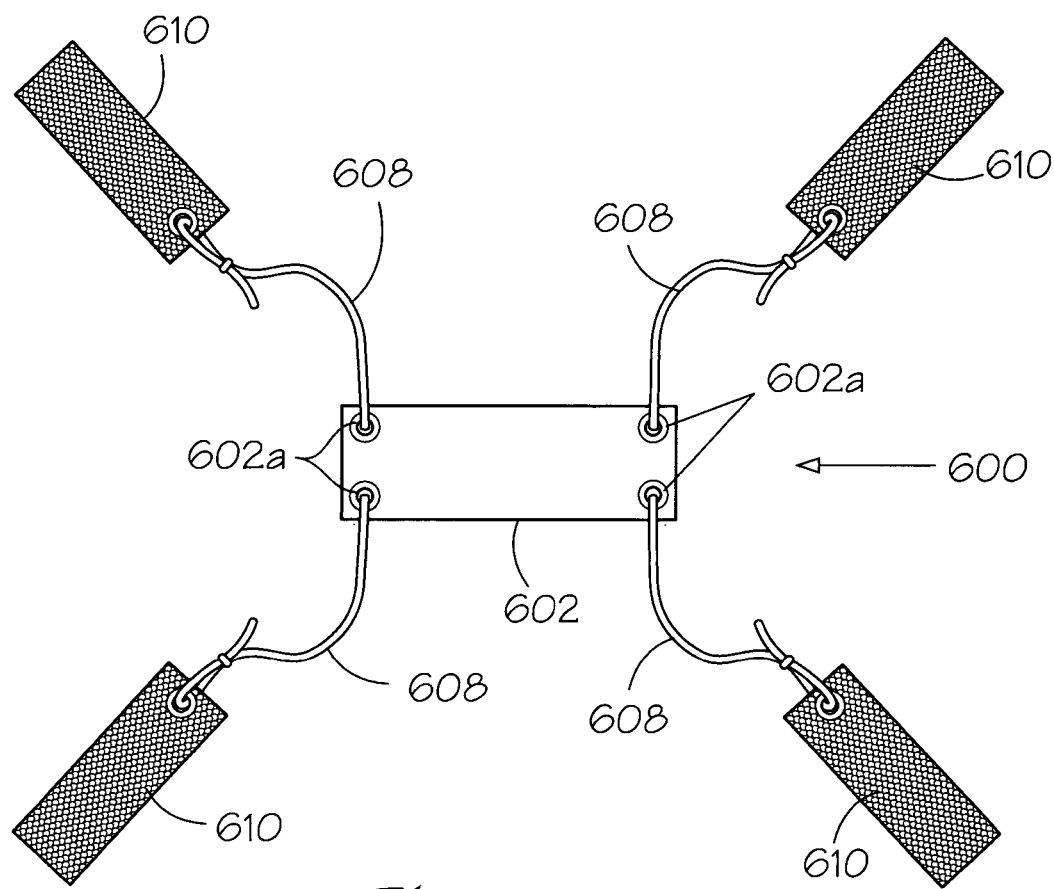
Figure 14D:
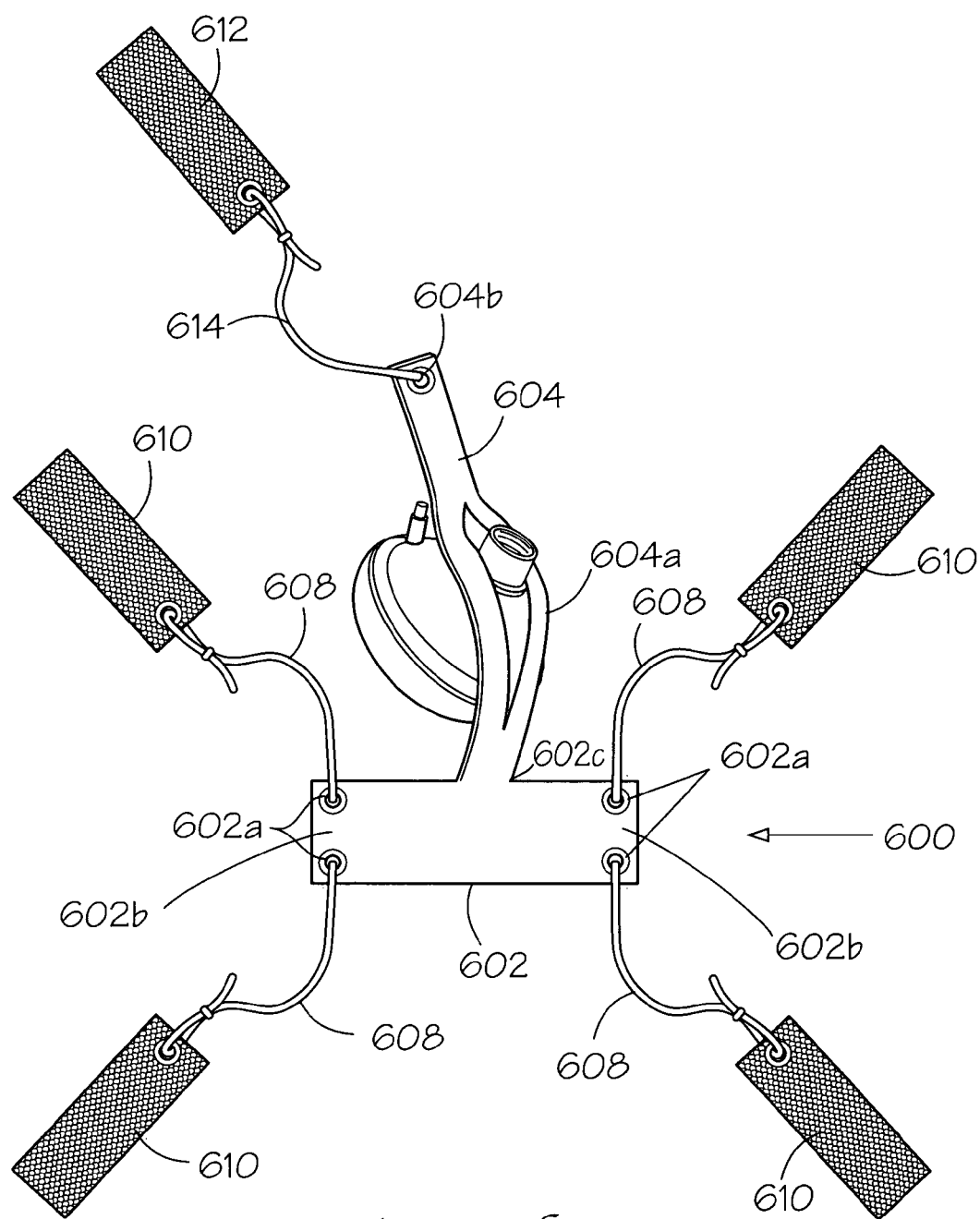
Figures 16A, 16B:
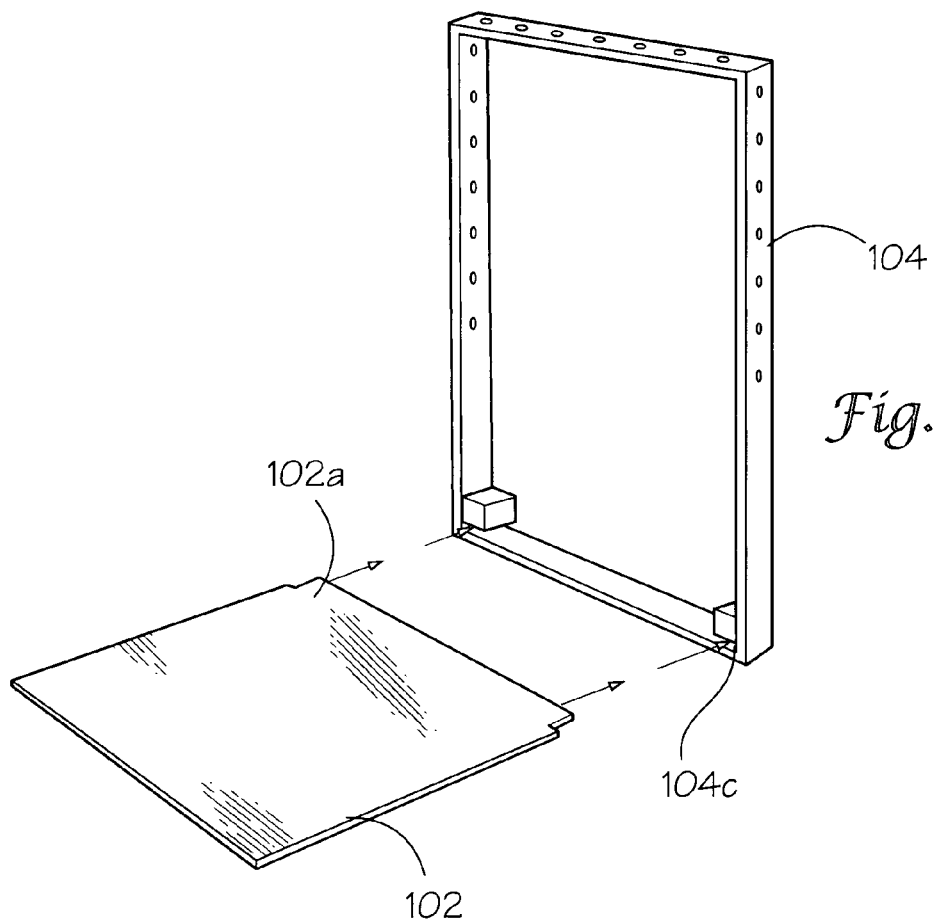
Figure 17A:
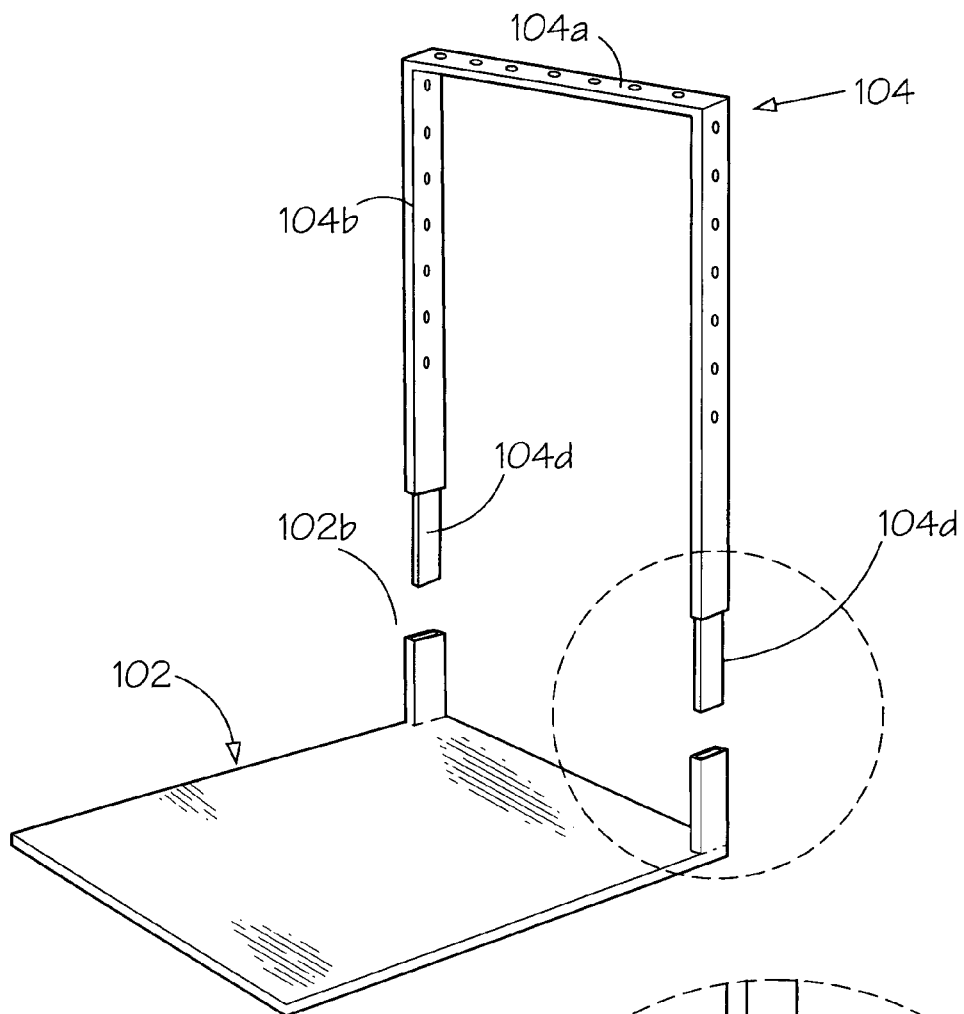
Figure 17B:
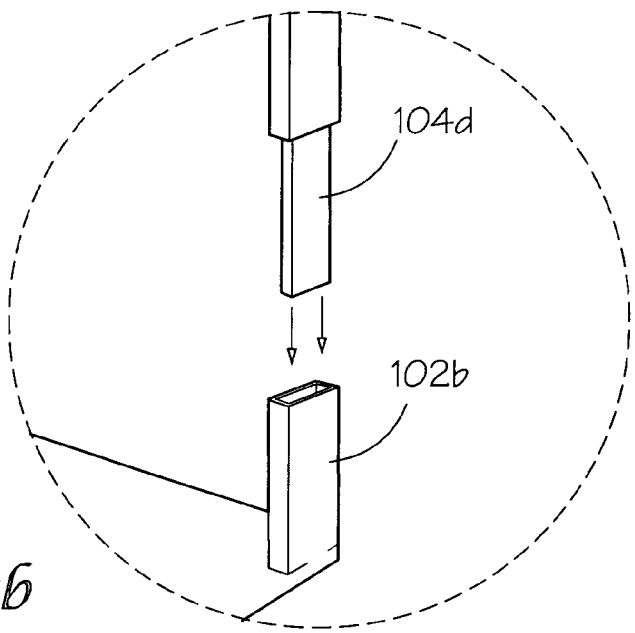
Figure 18:
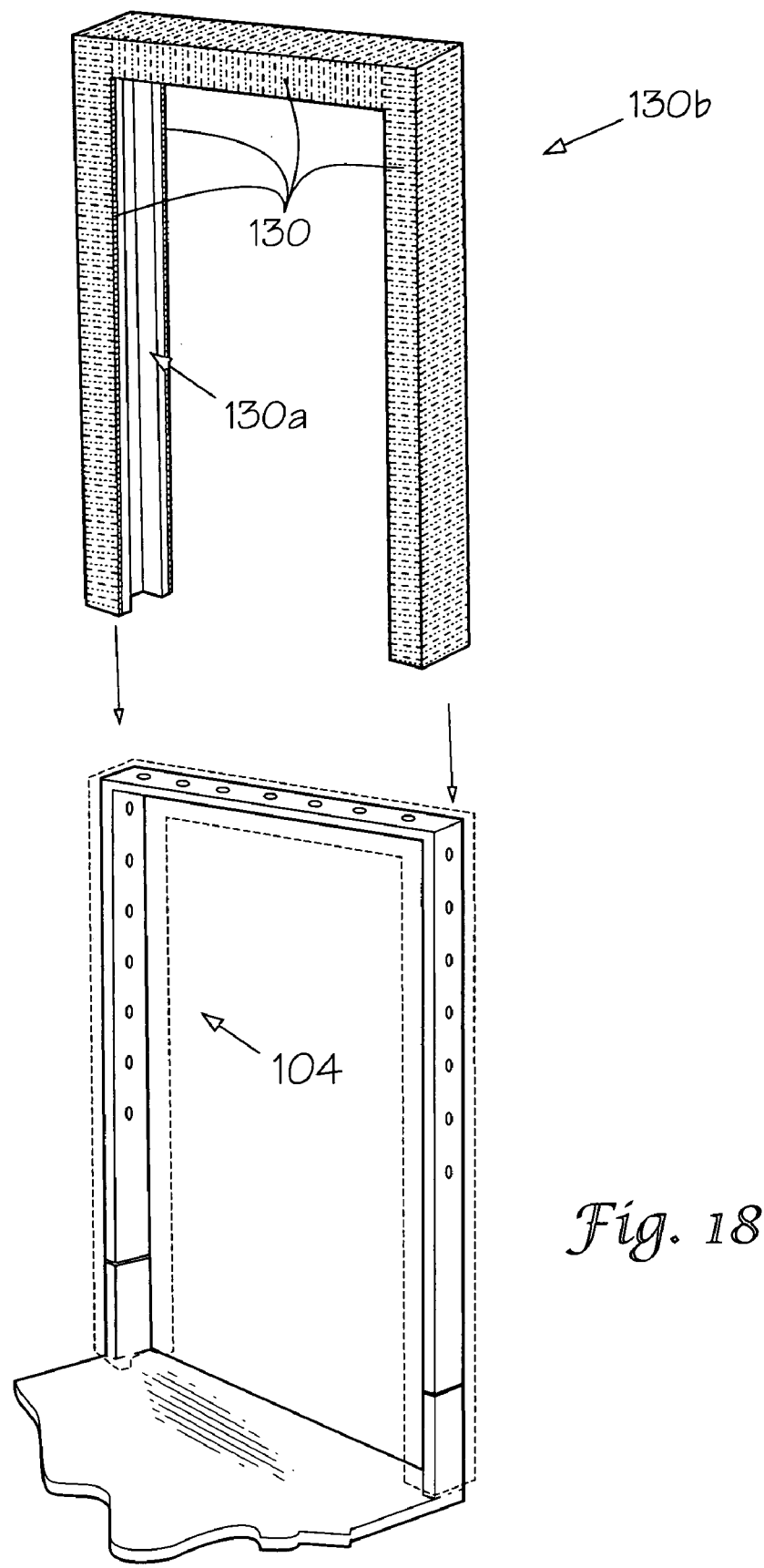

FIGS. 12b–c illustrate the harness of FIG. 12a in respectively loosened and tightened positions;

FIG. 12d shows the harness of FIGS. 12a–c in use with a patient in a supine position;

FIG. 13a shows the soft hook and loop attachment means of the present invention;

FIG. 13b shows the rigid hook and loop attachment means of the present invention;

FIG. 14a shows a hammock that is used with yet another embodiment of the present invention;

FIG. 14b shows the hammock of FIG. 14a in use with a patient in a supine position;

FIG. 14c shows a variation of the embodiment of FIG. 14a wherein the attachment means are fixed;

FIG. 14d shows the hammock of 14c further comprising of a middle strap that runs perpendicular from the hammock and the strap further defines a middle slit;

FIG. 15a–d illustrate yet another embodiment of the presently claimed invention further including two lateral plates;

FIG. 16a–b illustrate another embodiment of the present invention showing the support plate and the flat rectangular support base detached;

FIG. 17a–b shows a further embodiment of the presently claimed invention, highlighting how a support frame is attached to a support base; and FIG. 18 shows a U-shaped sleeve that is mounted on the support frame of the present invention.

DESCRIPTION

Figure 1:
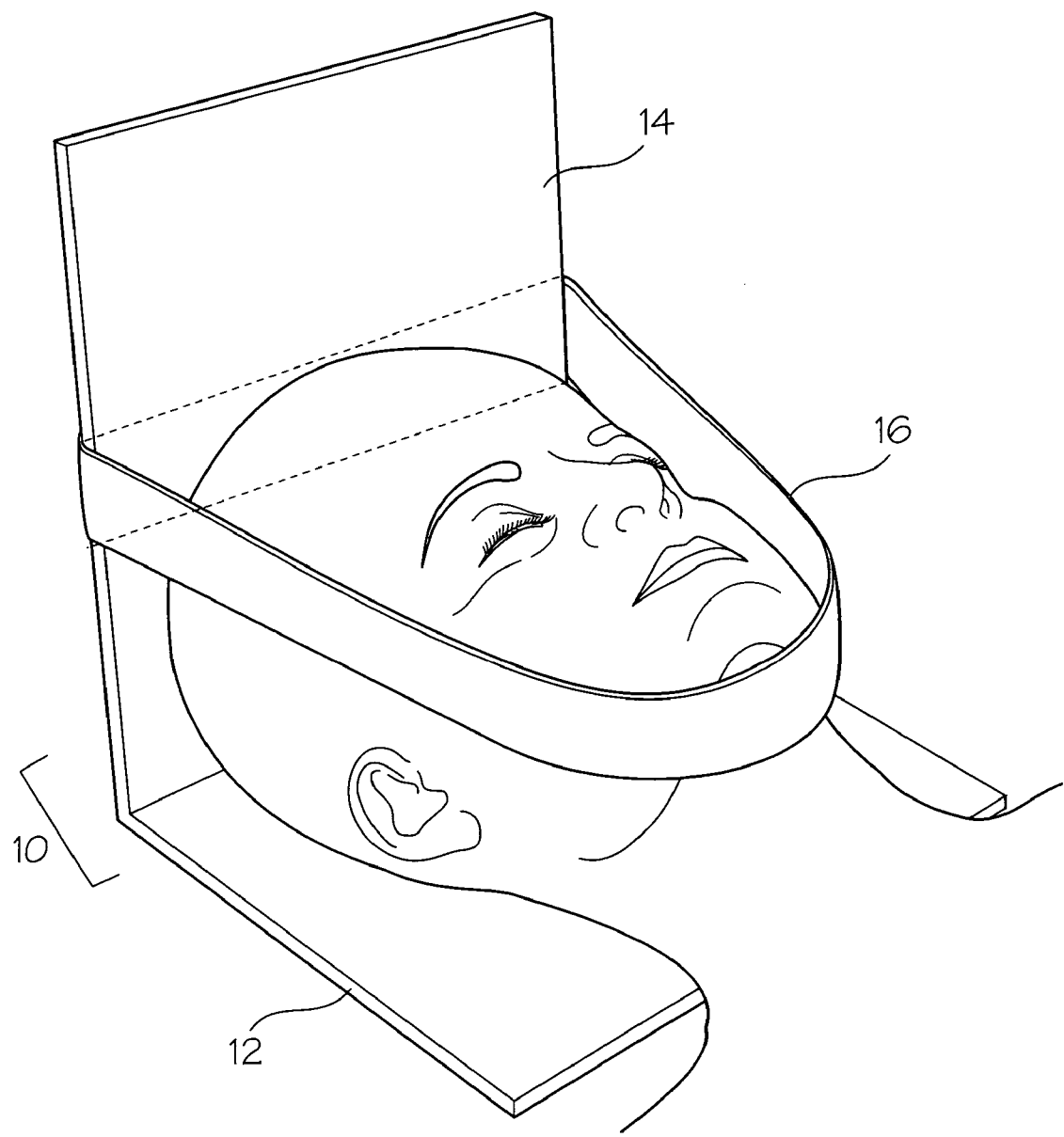
FIG. 1 shows a perspective view of the medical device in use with a patient in a supine position.

As shown in FIG. 1, a medical device used to overcome upper airway obstruction when a patient is in a supine position comprises a flat rectangular cradle 10 that has a first 12 and a second portion 14 wherein the first portion 12 has a length that is at least a distance that allows a patient's head to rest on and act as an anchor to the cradle and the second portion 14 is perpendicular to the first portion 12 and has a length that is at least a distance that allows a band 16 to be placed under a patient's chin and encircle the second portion 14 so that an upward pull can be generated on the chin by the band 16, and the cradle's width is at least a distance that allows for the clearance of a patient's side facial features when the patient's head rests on the first portion 12 of the cradle and a band 16 is made to encircle the chin of a patient and attach to the second portion 14 of the cradle; and a band 16 that attaches to the second portion 14 of the cradle when the second portion 14 is perpendicular to the first portion 12.

Figure 2:
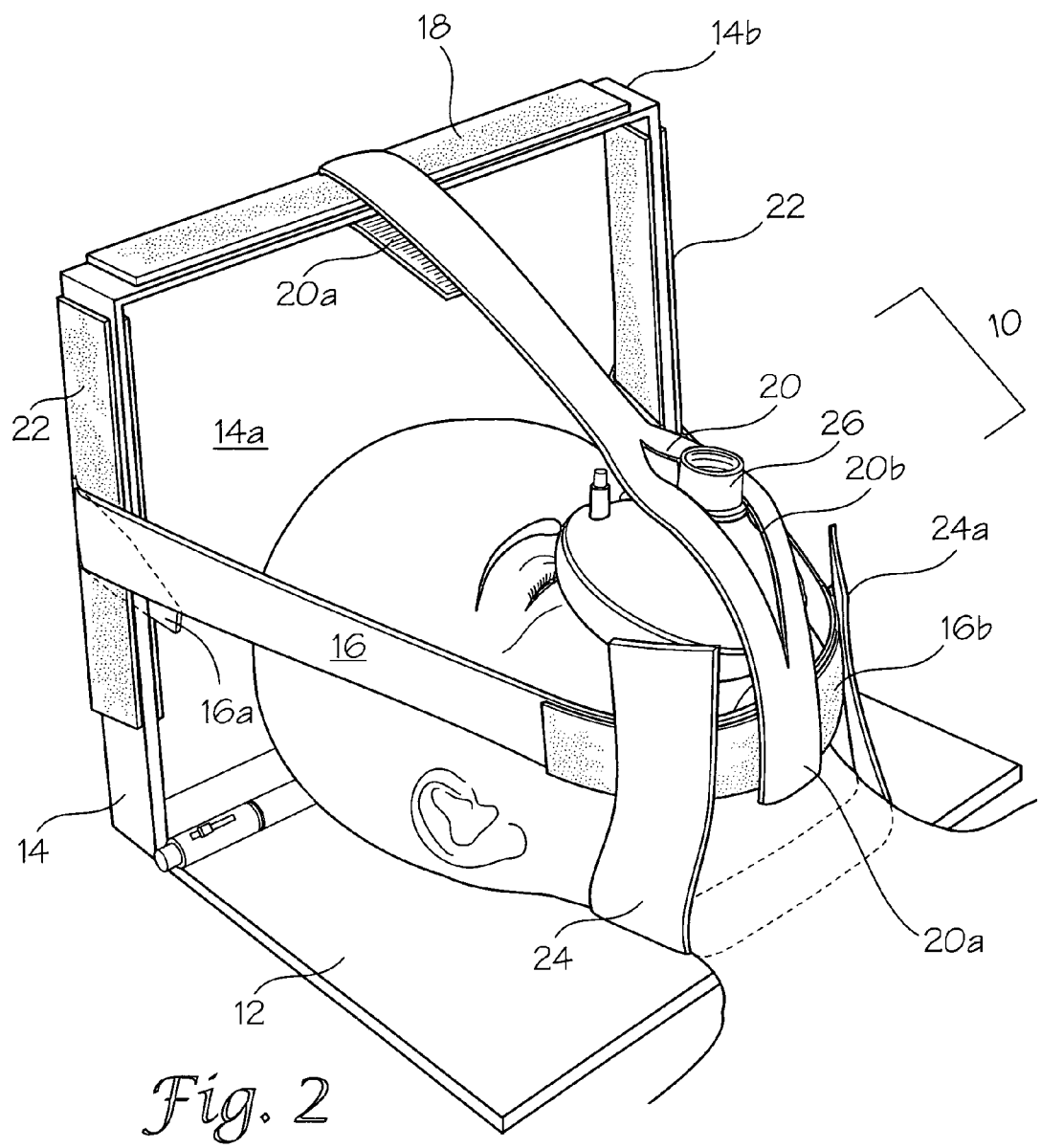
FIG. 2 shows a perspective view of another version of the medical device in use with a patient in a supine position.
Figure 3:
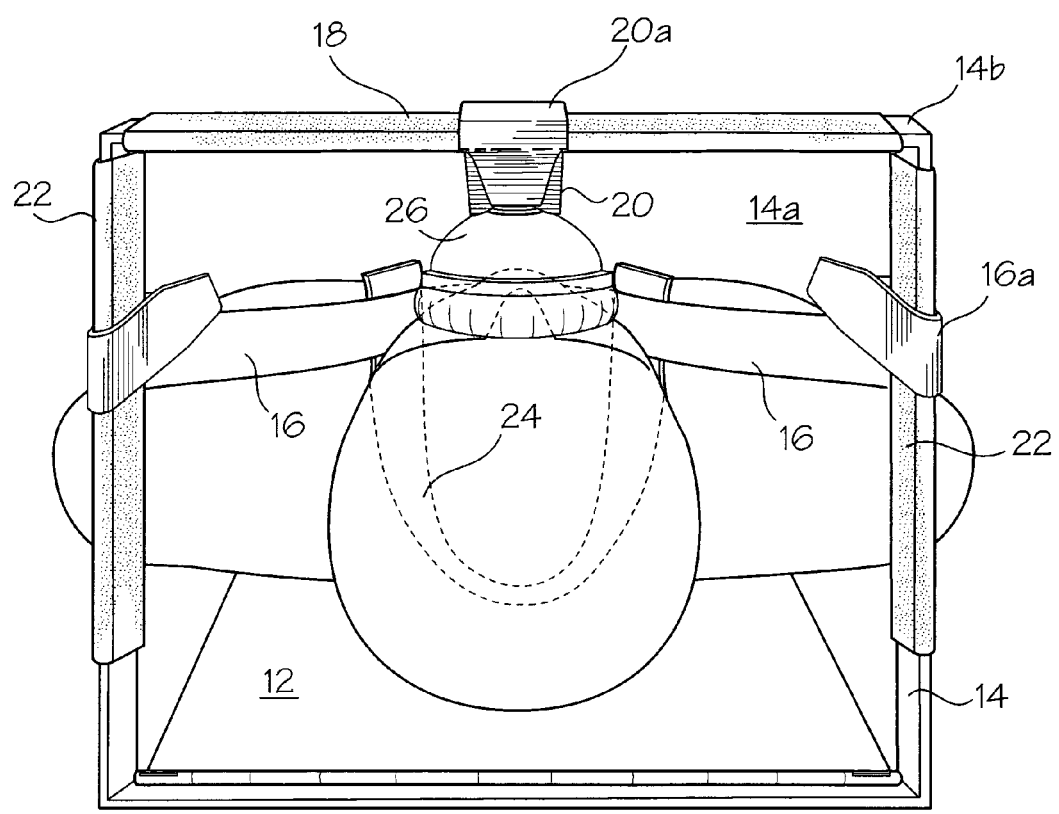
FIG. 3 shows a rear view of the medical device shown in FIG. 2, this view shows the second portion having an aperture within the second portion.

The cradle can be made of wood, stainless steel, plastics or polymers. The length of first 12 and second 14 portions of the cradle must be at least a 1 to 1 ratio. The length of the first portion 12 should be at least of a length that will allow a patients head to rest on it and act as an anchor to the medical device. The length of the second portion 14 should be of at least of a length that will create an upward pull on the chin of a patient when a band 16 is made to encircle the chin of the patient, when a patient is placed in a supine position, and the second portion 14 of the cradle 10. In a preferred embodiment of the invention, the length of the portions will be eight inches to twelve inches. Another embodiment of the invention has the first 12 and second 14 portions of the cradles being both eight inches in length. The width of the portions is to be at least eight inches, the preferred embodiment would have a width of twelve inches. The width has to be of sufficient length to allow for the clearance of the eyes when attaching the band 16 to the second portion 14 of the portion 10. As seen in FIG. 2 and FIG. 3, the second portion 14 of the cradle can define an aperture 14a that will merely make the second portion of the cradles a physical skeleton to attach the band 16 or straps yet to be defined.

The band can be made of an elastic material that has a degree of tension sufficient to pull the weight of a person's chin upward (when the patient is placed in a supine position) when encircling the second portion of the cradle and the chin of the patient. As seen in FIG. 2, the band 16 can also be made of fabric and have two ends, if the band 16 is made of fabric, then it is preferable that the ends of the bands 16a have either hook or pile fasteners. When using a fabric band 16, it is essential that the second portion 14 of the cradle have two receiving means 22 located on opposite sides of the second portion 14 and running along the length of the second portion 14 and situated a sufficient height to allow for an upward pull to be generated on the chin of a patient when the band 16 is placed around the chin of the patient and the ends of the band 16a are attached to receiving means 22 of the second portion 14 of the cradle. The receiving means 22 will also comprise of either hook or pile fasteners, depending on what type fasteners the ends of the band 16a utilize.

As seen in FIG. 2, the medical device can further comprise of having a middle attachment means 18 attached second portion 14 of the cradle (middle attachment means 18 can simply be glued on to the second portion 14), the middle attachment means 18 will attach to the second portion 14 at the outer extremity of the second portion 14a and be centered and run parallel along the width of the cradle 10. The attachment means 18 can be made of a fabric and contain hook or pile fasteners. The middle attachment means 18 is attached to a first strap 20, the first strap 20 has either hook or pile fasteners at its ends 20a (whether hook or pile fastener will depend on what type of attachment means the ends are connecting too). The first strap 20 will connect to the section (middle juncture) of the band 16b surrounding the chin of the patient using means known in the art (either hook or pile fasteners, this all depends on what type of fasteners the band has at the middle juncture of the band 16b to accommodate the connection). The first strap might define a first strap slit 20b running parallel along the length of the first strap. The first strap serves a duel purpose, the first purpose is to further apply upward pressure to the chin and the second purpose is to allow for the placement of a mask 26 within the slit that would cover the mouth and nose of the patient. The mask 26 would be used to provide either oxygen and/or an anesthetic to the patient.

The medical device can further comprise a second strap 24, the second strap 24 having attachment means located at the ends of the strap 24a (the attachment means would be either hook or pile fasteners). The second strap would encircle the rear of the patient's neck and would attach to the middle juncture of the band 16b fasteners. The only purpose for the second strap 24 is to secure the band 16 to the patient's chin, the invention does not require the second strap 24, it is used only as a safety precaution.

Figure 4:
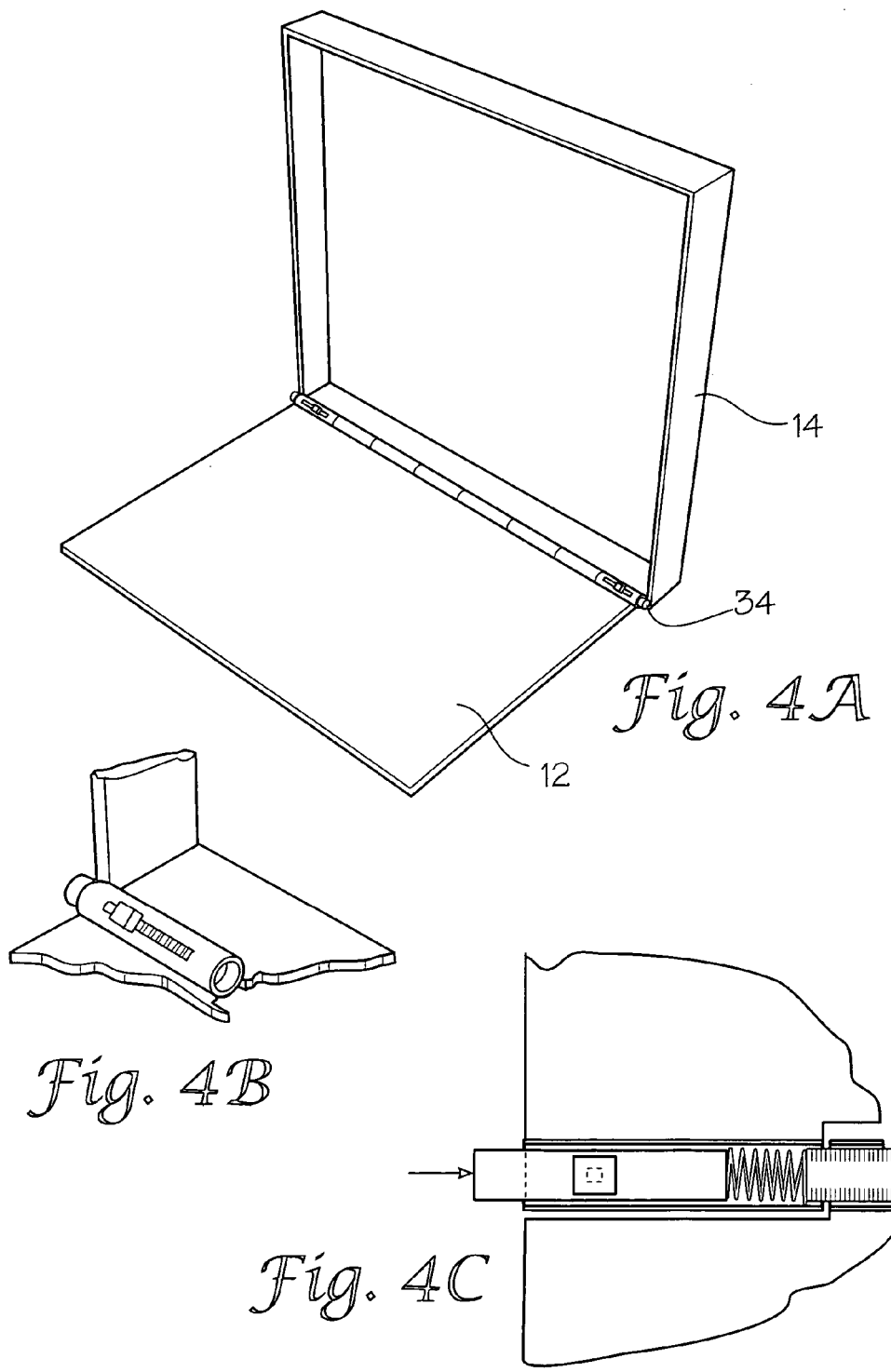
FIG. 4 shows a perspective view of another version of the present invention, this embodiment has a means for pivoting the portions and a locking means for maintaining the portions in a perpendicular position.
Figure 5:
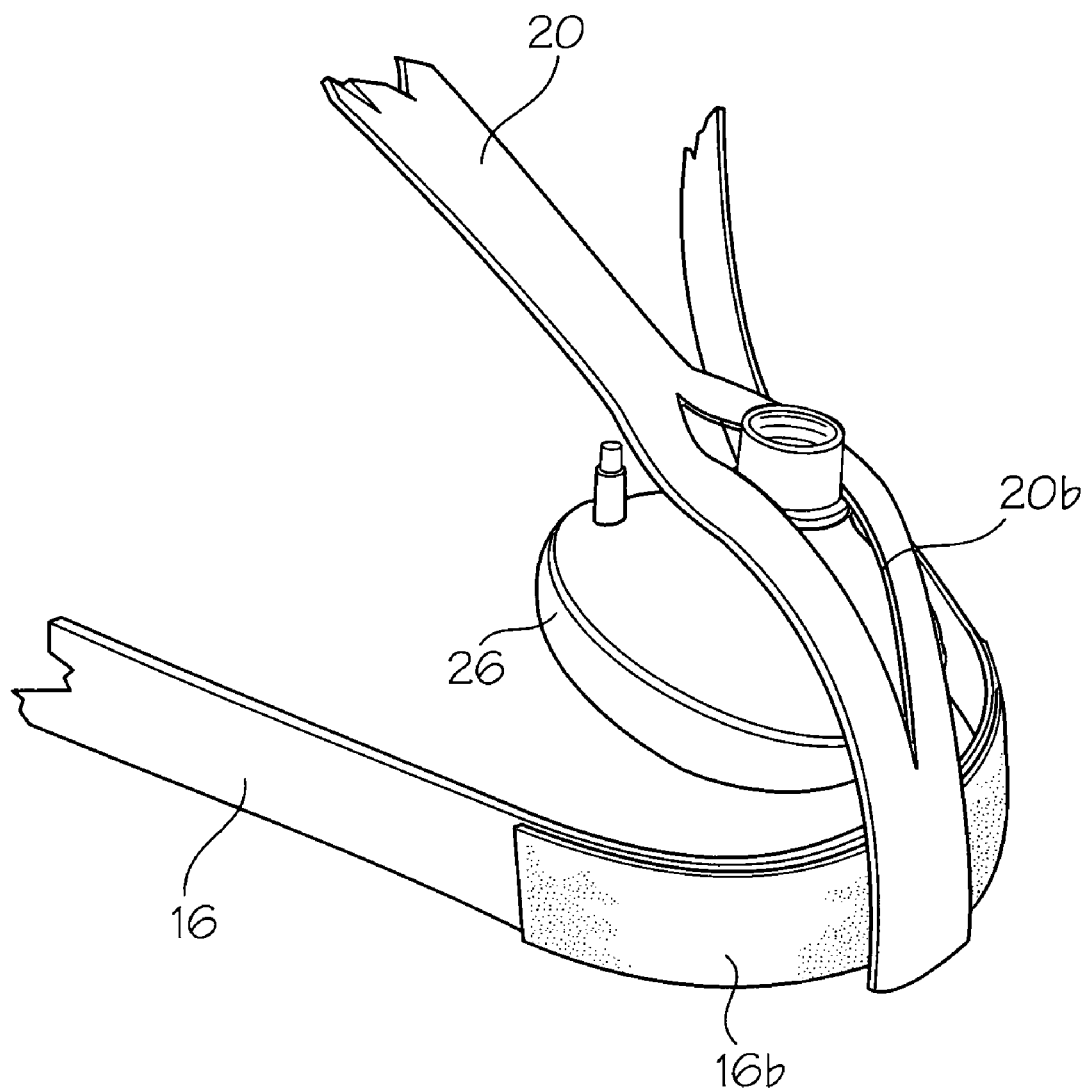
FIG. 5 shows a perspective of how the mask would attach to the first strap of the medical device and surround the nose and mouth of a patient in a supine position.

As seen in FIG. 4, another embodiment of the invention would comprise of a pivoting means 34 for folding the medical device. The pivoting means 34 would facilitate the transport of the device and would most likely be used in the field by emergency personnel, such as paramedics. The pivoting means 34 would connect the first 12 and second 14 portions of the cradles and have a closed locking position and an opening perpendicular locking position 36. The locking means would be incorporated into the pivot by means known in the art. As a safety precaution, the pivoting means, when placed in the perpendicular position would be placed so that they would not be able to rotate further than the perpendicular. This could simply be accomplished by inserting a screw along side the pivot (s) in either of the portions (allowing the head of the screw to be raised at least a few centimeters above the pivot) so that the portion not containing the screw could not be pivoted beyond the perpendicular. All of the previous elements discussed could be incorporated into this embodiment of the invention.

Figure 6:
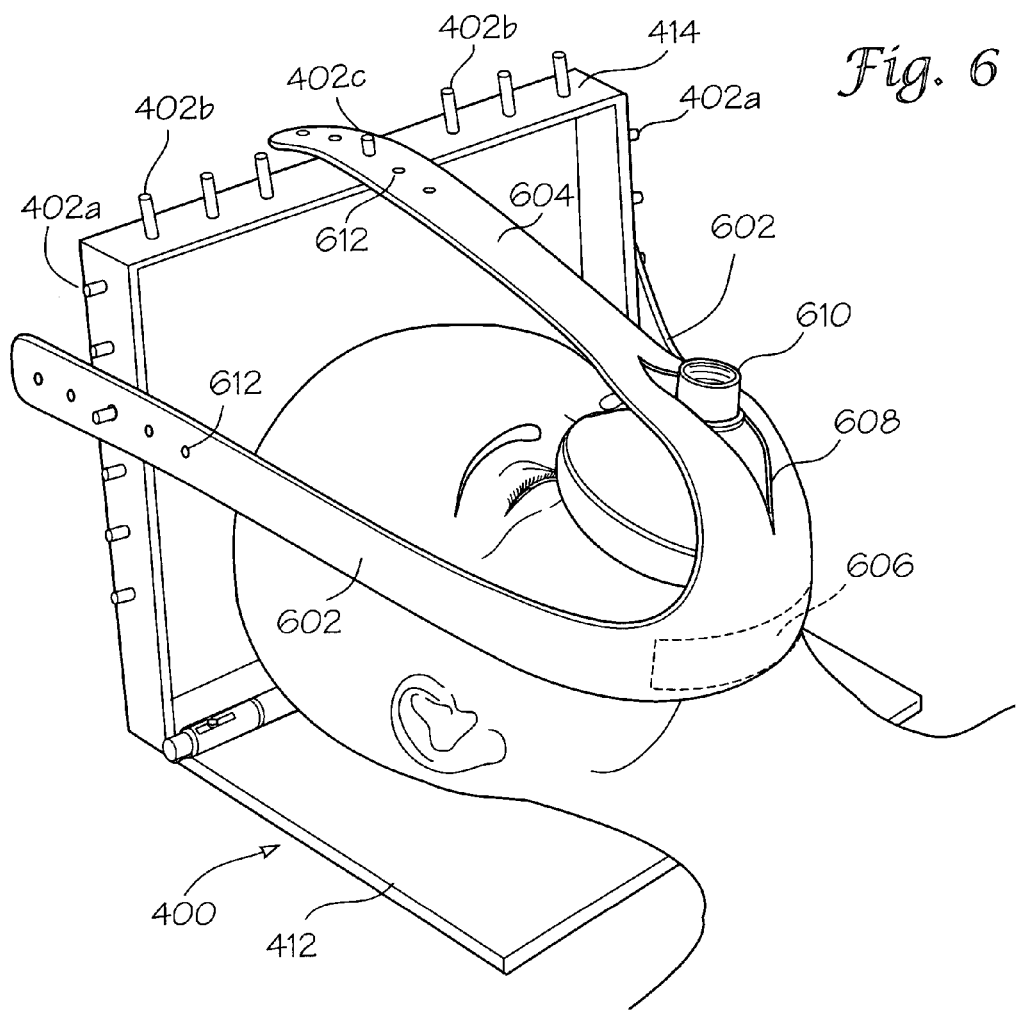
FIG. 6 shows a perspective view of another embodiment of the medical device in use with a patient in a supine position.

As shown in FIG. 6, in another embodiment of the medical device 400 used to overcome upper airway obstruction when a patient is in a supine position comprises a rectangular support base 412 that is attached to a support frame 414 by the pivoting means described above; and a T-band 600, as illustrated in FIG. 7, that attaches to the support frame 414 when the T-band 600 is placed around the chin of a patient when the medical device 400 is used.

The support frame 414 having a middle rod 402c that is located in the middle of the superior edge of the support frame 414 and six superior rods 402b located on the superior edge of the support frame 414, the superior rods 402b are positioned so that they are equally spaced from the middle rod 402c and run toward the outer edges of the support frame 414 in increments of one inch starting from the middle rod 402c outward, more specifically, three superior rods 402b are placed on each side of the middle rod 402c. The middle rod 402c measuring at least 1/8 of an inch in diameter and 1/4 of an inch in height. Each superior rod 402b measuring at least 1/8 of an inch in diameter and 3/4 of an inch in height. The support frame 414 further having 10 lateral rods 402a positioned on the lateral edges of the support frame 414, wherein the first of the lateral rods 402a is placed two inches from the superior edge of the support frame 414 and the remaining lateral rods 402a are positioned a distance of one inch from each other, more specifically, five lateral rods 402a are placed on each of the vertical sides of the support frame 414. Each lateral rod 402a measuring at least 1/8 of an inch in diameter and 1/4 of an inch in height. In this embodiment of the invention, the superior edge of the support frame 414 shall have a length of 8 inches and the lateral edges of the support frame 414 having a length of twelve inches.

Figure 7:
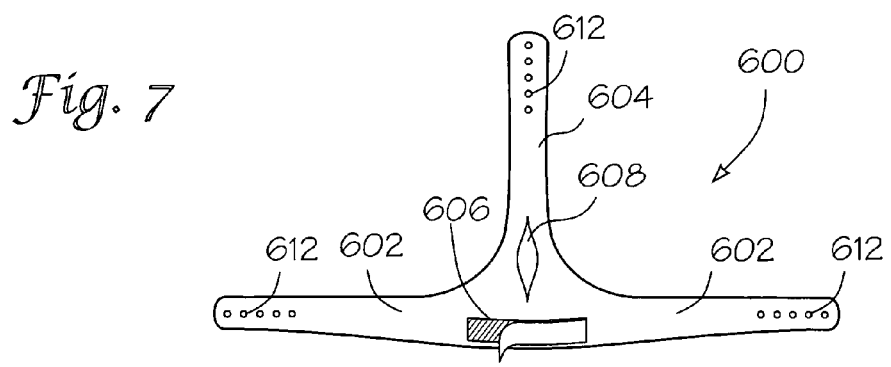
FIG. 7 shows a bottom view of the t-band piece of the medical device.
Figure 8:
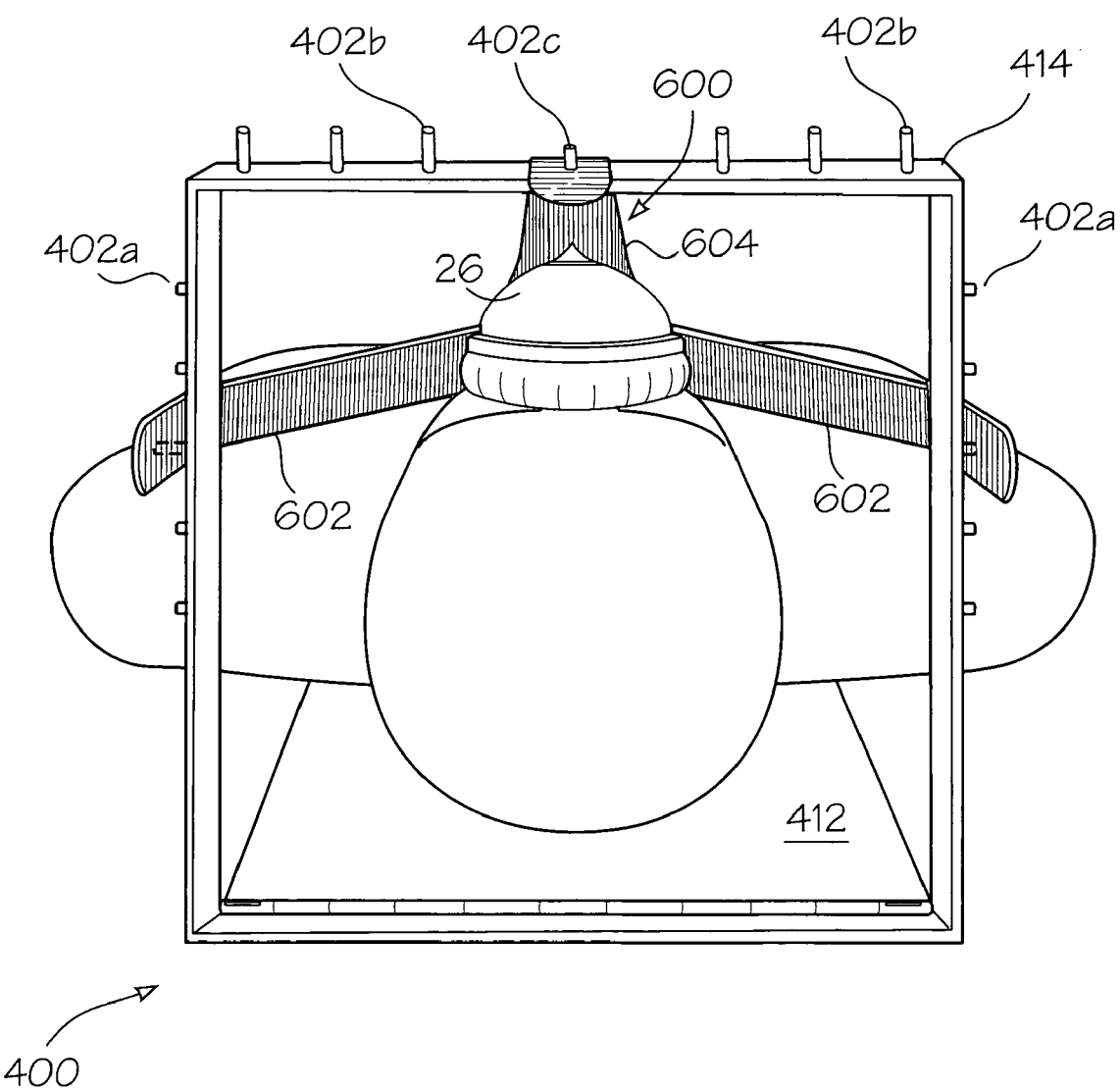
FIG. 8 shows a rear view of the medical device shown in FIG. 7.
Figures 9, 10:
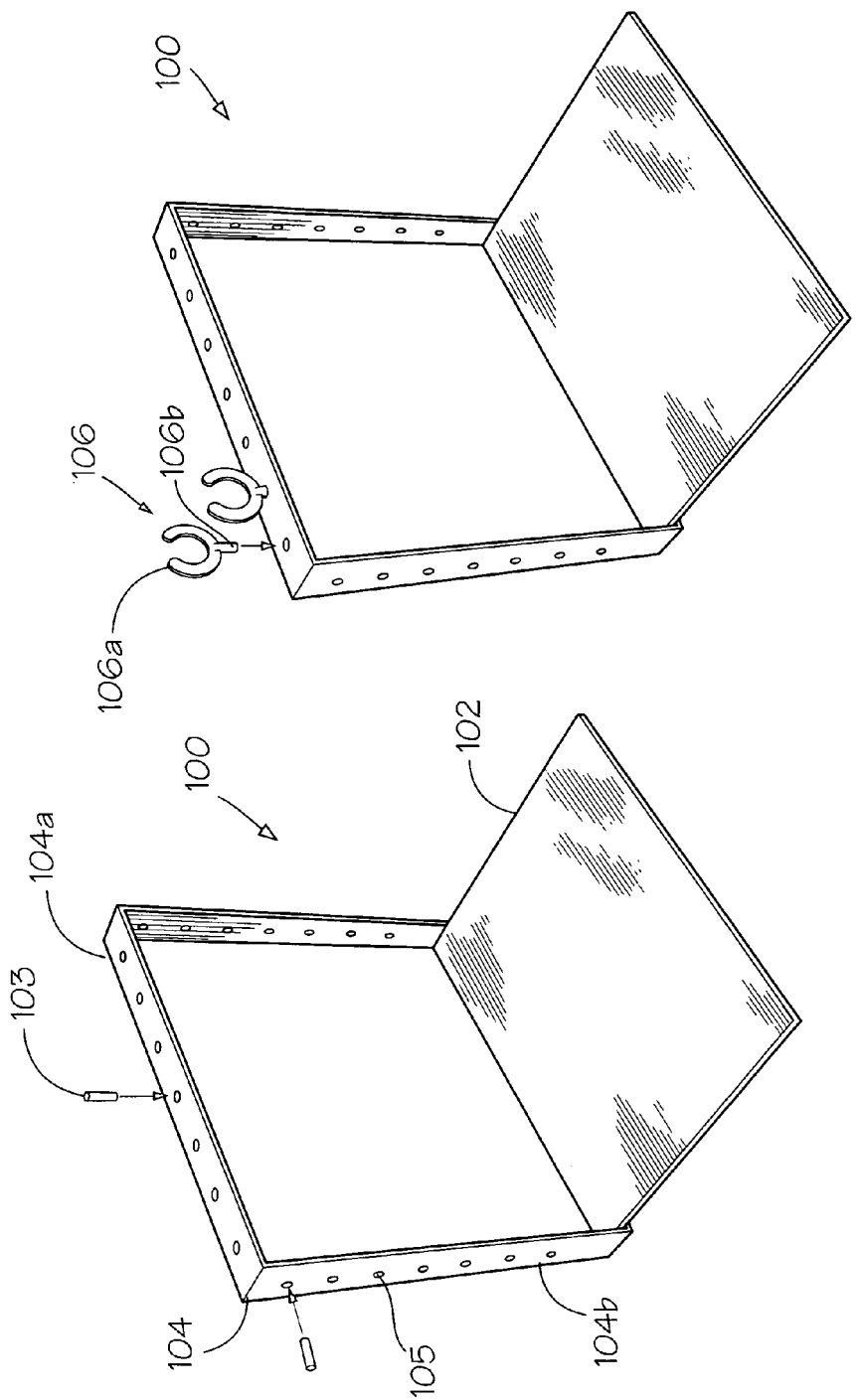
FIG. 9 shows a perspective view of another version of the medical device of the present invention with a peg and hole configuration.
FIG. 10 shows a perspective view of another version of the medical device of the present invention with an attachable anesthesia hose support for accommodating an anesthetic hose.

As shown in FIG. 7, the T-band 600 is a three sided strap, wherein two sides 602 of the strap are perpendicular to a middle side 604 of the strap and each side strap 602 measures at least 12½ inches from where each side strap junctions with the middle strap 604. The middle strap shall measure at least 13½ inches from where the middle strap 604 junctions to the side straps 602. Each of the straps of the T-band 600 is at least 1¼ inches in width. The T-band 600 further defines a middle slit 608 that is defined within the middle strap 604 and runs from the junction of the straps toward the end of the middle strap 604, the middle slit 608 being at least 5½ inches in length. All of the straps shall define at least six fenestrations 612 starting one inch from the end of each strap and each fenestration 612 being ½ an inch apart from each other, each fenestration shall be at least 3/16 of an inch in diameter. The T-band 600 might further comprise an adhesive layer 606 that is placed at the junction of the T-band 600 so that the band bonds with the chin of patient when using the medical device 400.

A method of overcoming upper airway obstruction when a patient is in a supine position comprises the steps of placing the above mentioned medical device 10 on a flat surface, resting the back of a patient's head on the first portion 12 of the cradle, and encircling the chin of the patient with the band 16 and attaching the rest of the band to the second portion 14 of the cradle, the band's attachment to the second portion 14 would be in a position sufficiently high so that an upper pull can be generated on the chin of the patient.

The above method describes the most rudimentary use of the medical device described in this application. The medical device's main purpose is to prevent the blockage of the upper airway. As stated before, this is accomplished by pulling the chin up and away from the body. The band 16 pulls the chin upward and the second portion 14 of the cradle is used to ensure that the pressure applied to the chin is maintained while freeing the hands of the practitioner. The medical device can also be used as means to secure a mask 26 to the face of a patient.

In another embodiment of this invention, As seen in FIGS. 9–11c, the medical device 100 used to overcome upper airway obstruction when a patient is placed in a supine position comprises a flat rectangular support base 102, a support frame 104 having superior 104a and lateral 104b sides attached perpendicularly to the flat rectangular support base 102, wherein the superior 104a and lateral sides 104b of the support frame 104 define a plurality of holes 105, a plurality of pegs 103 inserted into the holes 105 of the support frame 104, a T-band 110 attached to the pegs 103 inserted to the support frame 104 when the T-band 110 is placed around the chin of a patient, wherein the T-band 110 has a hook and loop material 110a (not seen in FIG. 11c) fixedly placed on the cross section of the T-band 110 that is placed around the chin of the patient, and a chin pad 108 having two sides, wherein one side is made of adhesive material and the other side having a loop and hook material, the chin pad's 108 side with the hook and loop material attaches to the cross section of the T-band 110a having the hook and loop material prior to placing the T-band 110 around the chin of the patient.

The embodiment of FIGS. 9–11c can further comprise of an anesthesia hose support 106 having a peg side 106b and a support side 106a, wherein the anesthesia support peg side 106b is inserted into one of the holes 105 of the superior side 104a of the support frame 104.

The embodiment of FIGS. 9–11c can further comprise of two lateral plates as seen in FIGS. 15a–15d, each lateral plate 120 having two sides, a flat side 120b and a U-shaped side 120a, that slide along the lateral sides 104b of the support frame 104 and run flush with the lateral sides of the support base 102, until the U-shaped side 120a of the lateral plates is flush with the lateral sides 104b of the support frame 104. The plates may be made of stainless steel or any other material known in the medical field.

A method of using the invention in FIGS. 9–11c, which comprises the steps of first placing a patient's head on the rectangular support base 102, then placing a chin pad 108 around the chin of the patient so that the hook and loop material of the chin pad does not face the chin of the patient, then placing the cross section 10a of the T-band 110 around the chin pad 108, and lastly, attaching the ends of the T-band 110 to the support frame 104 so that an upper pull is created on the lower jaw of the patient.

Yet another embodiment of the invention is seen in FIGS. 12a–d, the medical device 100 used to overcome upper airway obstruction when a patient is placed in a supine position comprises a flat rectangular support base 102, a support frame 104, having superior 104a and lateral 104b sides, attached perpendicularly to the flat rectangular support base 102, wherein the superior 104a and lateral sides 104b of the support frame 104 define a plurality of holes 105, a harness 200, having a headband section 202, the headband section 202 having a front 202a and a rear 202b section, and two belt sections 204, each belt section 204 having a fixed end 204a and an adjustable end 204b, wherein the headband section 202 defines two apertures 202c in the rear of the headband 202b section and further comprises of two tension strips 206, each tension strip 206 having a fixed end 206a and an adjustable end 206b, wherein the fixed ends 206a of the tension strips 206 are attached on the headband section 202 at locations that are flush with the outer sides of the apertures 202c and the tension strips 206 run toward the front 202a of the headband section 202, and wherein each belt section 204 is fixedly attached to the front section 202a of the headband section 202 and the belt sections 204 are further fixedly attached to each other to form an x-junction 204c between the belt sections 204 and wherein the adjustable ends of the belt sections 204b are threaded through the apertures 202c of the headband section 202, the adjustable ends of the belt sections 204b of the harness 200 attach to the lateral sides 104b of the support frame 104. In the above embodiment, the adjustable ends of the belt sections 204b of the harness 200 comprise of hook and loop materials. The adjustable ends 206b of the tension strips 206 attach to receiving headband sections 202d using hook and loop materials. Other methods of attaching the adjustable ends of the belt section 204b of the harness 200 to the support frame 104b and the tension strips 206 to the headband 202 are well known in the art.

The embodiment of FIGS. 12a–d can further comprise of two lateral plates as seen in FIG. 15a–15d, each lateral plate 120 having two sides, a flat side 120b and a U-shaped side 120a, that slide along the lateral sides 104b of the support frame 104 and run flush with the lateral sides of the support base 102, until the U-shaped side 120a of the lateral plates is flush with the lateral sides 104b of the support frame 104. The plates may be made of stainless steel or any other material known in the medical field.

The above embodiment of the invention can further comprise of an anesthesia hose support 106 having a peg side 106b and support side 106a, wherein the anesthesia support peg side 106b is inserted into one of the holes 105 of the superior side of the support frame 104a.

A method of using the invention in FIGS. 12a–d, which comprises the steps of first placing a harness 200 around the head of a patient so that the adjustable ends 204b of the belts of the harness 200 flow from the back of the neck of the patient, next, resting the back of the patients head on the support base 102, then, pulling the adjustable ends 204b of the belts and then crossing them under the lower jaw of the patient so that an upward pull is created on the lower jaw of the patient, and lastly securing the adjustable ends 204b of the belts of the harness 200 to the lateral sides of the support frame 104b.

A further embodiment of the current invention is seen in FIGS. 13a–14b, the medical device 300 used to overcome upper airway obstruction when a patient is placed in a supine position comprises a flat rectangular support base 102, a support frame 104 having superior 104a and lateral 104b sides attached perpendicularly to the flat rectangular support base 102, wherein the superior 104a and lateral sides 104b of the support frame 104 define a plurality of holes 105, a hammock 302, the hammock 302 comprising of a chin support 304, two cables 306, and four cable attachment means 308, wherein the chin support 304 defines two tubular channels 304a on the chin support's lateral sides, and wherein each cable 306 is strung through each tubular channel 304a so that each cable's end flow from each side of the tubular channel 304a, and wherein each attachment means 308 attaches to each end of the cables 306, and each of the cable's attachments means 308 of the hammock 302 attach to the lateral sides 104b of the support frame 104 so that each cable 306 solely touches one side of the lateral support frame 104b.

The hammock of FIGS. 14a–b can comprise of another embodiment, as seen in FIGS. 14c–d, wherein a hammock 600, comprises of a rectangular chin support 602, having a midpoint 602c and two ends 602d, four cables 608, and four cable attachment means 610, wherein the chin support 602 defines four apertures 602a located on each of the corners of the hammock, and wherein each cable 608 is secured to the hammock 602 at each aperture 602a location by means known in the art, and wherein each cable attachment means 610 attaches to each end of the cables 608, and each of the cable's attachments means 610 of the hammock 602 attach to the lateral sides 104b of the support frame 104. This embodiment can further comprise of the harness having a middle strap 604 running perpendicularly from a midpoint of the harness 602, the middle strap 604 having a middle slit 604a, and the middle strap 604 further defining a strap aperture 604b on the end not connected to the harness 602, a strap cable 614 is secured to the strap aperture 604b by means known in the art, a strap cable attachment means 612 attached to the strap cable 614, and the strap cable attachment means attaches to the superior side of the support frame 104a.

As seen in FIG. 13a, this embodiment can further comprise of four flexible receiving attachment means 309, each receiving attachment means 309 having a securing end 309b and a receiving end 309a, both ends made of hook and loop material, wherein the four flexible receiving attachment means 309 are secured around the lateral sides of the support frame 104b so that each lateral support frame 104b is attached to two of the flexible receiving attachment means 309, and wherein each receiving end 309a of the receiving attachment means 309 attaches to each of the cable's attachment means 308.

As seen in FIG. 13b, this embodiment can further comprise of four rigid receiving attachment means 310, each receiving attachment means 310 having a U-joint end 310a and a receiving end 310b, the receiving end 310b comprising of a hook and loop material, wherein the four rigid receiving attachment means 310 are placed on the lateral sides of the support frame 104b so that each lateral support frame 104b is attached to two of the rigid receiving attachment means 310, and wherein each receiving end 310b of the receiving attachment means 310 attaches to each of the cable's attachment means 308.

In a preferred embodiment of the above invention, the receiving ends 310b of the receiving attachments means 310 and each of the cable's attachment means 308 are made of a hook and loop material.

The embodiment of FIGS. 13a–14b can further comprise of two lateral plates as seen in FIGS. 15a–15d, each lateral plate 120 having two sides, a flat side 120b and a U-shaped side 120a, that slide along the lateral sides 104b of the support frame 104 and run flush with the lateral sides of the support base 102, until the U-shaped side 120a of the lateral plates is flush with the lateral sides 104b of the support frame 104. The plates may be made of stainless steel or any other material known in the medical field.

The embodiment of the invention shown in FIGS. 13a–14b can further comprise of an anesthesia hose support 106 having a peg side 106b and support side 106a, wherein the anesthesia support peg side 106b is inserted into one of the holes 105 of the superior side of the support frame 104a.

A method of using the invention in FIGS. 13a–14b, which comprises the steps of first placing a patient's head on the rectangular support base 102, next placing the chin support 304 of the hammock 302 around the lower jaw of a patient so that tubular channels 304a of the chin support 304 are approximately parallel to the sides of the face of the patient, and lastly, adjusting the cable's attachment means 308 so that when the cable's attachment means 308 are attached to the support frame 104b of the medical device 300, an upward pull is created on the lower jaw of the patient.

The inventions of FIGS. 9–15d, as seen in FIG. 16a–16b, might further comprise the flat rectangular support base 102 having an insertion side 102a on the flat rectangular support base 102, and the support frame 104 further defining a reception site 104c on each of the lateral sides of the support frame 104, wherein the insertion side of the flat rectangular support base 102a is inserted within the reception site 104c of the support frame 104.

In another embodiment of the present inventions, as seen in FIGS. 17a–b, the flat rectangular support base 102 has two vertical reception extensions 102b, wherein each vertical reception extension 102b is located on each corner of the one side of the flat rectangular support base 102, and the support frame lateral side's free ends 104d are inserted within the vertical reception extensions 102b.

In yet a further embodiment of the present inventions, as seen in FIG. 18, a U-shaped sleeve 130, having an inner 130a and an outer side 130b, is mounted on the support frame 104, wherein the outer side 130b of the sleeve is made of hook and loop material and the inner side 130a of the sleeve 130 is made of a rigid material.

An advantage of the present invention is that a patient's eyes are never in danger of being damaged, for when the band is placed to encircle the chin of the patient and then attached to the second portion of the cradle, the band attaches to the second portion of the cradle at a position that does not allow the band to rub against the eyes.

Another advantage of the present invention is that when using the embodiment that defines an aperture in the second portion of the cradle, a patient can be monitored from behind the patient, there is no obstruction to seeing the patient.

A further advantage of the present invention is that it is compact and rudimentary in its nature. The device can be made operational by simply placing the device on a flat surface, placing a patient's head on the device (the patient being in a supine position) and encircling an elastic band around the patient's chin and the second portion of the cradle.

An advantage of using the invention of FIGS. 9–11c is that it allow medical personnel to have a choice where to attach the T-band's ends to the support frame of the medical device. This variation of the present invention also grants medical personnel the ease of securing an anesthetic hose or any other types of attachable devices to any side of the support frame. An advantage of using the chin pad is that it improves the traction of the T-band when exerting force on the lower jaw, thereby preventing the T-band from slipping from the lower jaw. A further advantage of the chin pad is that it protects the skin of the lower jaw from the trauma caused by the contact with the band.

An advantage of using the invention of FIGS. 12a–d is that the harness is secured to the head of the patient thereby reducing the displacement that is generated when pulling on the skin of the lower jaw when attaching the harness to the support frame. By crossing the adjustable ends of the belt of the harness below the lower jaw, a force of upward pressure is created within the belts so that a greater force of traction is applied to the skin of the lower jaw at the x-junction of the bands, when an upward pulling force is applied to the ends of the harness belts when securing to belts to the support frame.

An advantage of using the invention of FIGS. 13a–b is the simplicity of its use and the hammock's low cost of production. The configuration of the cables with relation to the support frame when the patient is placed in traction prevents the hammock from slipping of the lower jaw of the patient.

When using the two lateral plates, all of the above inventions have the advantage of allowing medical personnel to stabilize the head of a patient, while providing upper airway management, when transporting a patient.

An advantage of using the detachable support base and the support frame with the current invention is that it allows for ease in portability, transport, and storage.

Yet a further advantage to the device is that it does not require attachment to other structures to become operational, it is the ideal device for practitioners working in the field, paramedics.

Another advantage of the invention is the simplicity in which it can be taken off a patient should an emergency situation arise, one would simply detach the band by pulling off the hook and pile fasteners.

An advantage of using the embodiment of FIG. 18, is that it promotes sterility, for the U-shaped sleeve can be disposable.

Finally, another advantage of this device is that it frees the hands of the operator, thereby allowing the attendant to treat other problems that the patient might be experiencing and to attend to other patients.

Although the present invention has been described in considerable detail with reference to certain preferred versions thereof, other versions are possible. Therefore the spirit and the scope of the claims should not be limited to the description of the preferred versions contained herein.

What is claimed is:

1. A medical device used to overcome upper airway obstruction when a patient is placed in a supine position comprising:
   a flat rectangular support base;
   a support frame having a superior and lateral sides, and the support frames lateral sides attach perpendicularly to the flat rectangular support base, wherein the superior and lateral sides of the support frame define a plurality of holes;
   a plurality of pegs inserted into the holes of the support frame;
   a T-band attached to the pegs inserted to the support frame when the T-band is placed around the chin of a patient, wherein the T-band has a hook and loop material fixedly placed on the cross section of the T-band that is placed around the chin of the patient; and
   a chin pad having two sides, wherein one side is made of an adhesive material and the other side having a loop and hook material, the chin pad's side with the hook and loop material attaches to the cross section of the T-band having the hook and loop material prior to placing the T-band around the chin of the patient.

2. The medical device of claim 1, wherein the flat rectangular support base has an insertion side on the flat rectangular support base, and the support frame has a reception site on each of the lateral sides of the support frame, wherein the insertion side of the flat rectangular support base is inserted within the reception site of the support frame.

3. The medical device of claim 2, further comprising an anesthesia hose support having a peg side and support side, wherein the anesthesia support peg side is inserted into one of the holes of the superior side of the support frame.

4. The medical device of claim 3, further comprising two lateral plates, having two sides, a flat side and a U-shaped side, that slide along the lateral sides of the support frame and run flush with the lateral sides of the support base, until the U-shaped side of the lateral plates is flush with the lateral sides of the support frame.

5. The medical device of claim 1, wherein the flat rectangular support base has an insertion side on the flat rectangular support base, and the support frame has a reception site on each of the lateral sides of the support frame, wherein the insertion side of the flat rectangular support base is inserted within the reception site of the support frame.

6. The medical device of claim 5, further comprising two lateral plates, having two sides, a flat side and a U-shaped side, that slide along the lateral sides of the support frame and run flush with the lateral sides of the support base, until the U-shaped side of the lateral plates is flush with the lateral sides of the support frame.

* * * * *